United States Patent [19]

Kelly et al.

[11] 4,083,364
[45] Apr. 11, 1978

[54] HEAD MOUNTED ANIMAL INFORMATION MEANS

[76] Inventors: L. Thomas Kelly, 603 W. 200 14th St., Carson, Calif. 90745; Robert R. Beachler, Jr., 89 Buckskin La., Rolling Hills Estates, Calif. 90274; Tor H. Petterson, 31248 Palos Verdes West, Palos Verdes Peninsula, Calif. 90274

[21] Appl. No.: 672,669

[22] Filed: Apr. 1, 1976

Related U.S. Application Data

[63] Continuation-in-part of Ser. No. 580,488, May 23, 1975, abandoned.

[51] Int. Cl.² .................. A61B 5/02; A61B 10/00; G01K 1/02
[52] U.S. Cl. .................. 128/2 H; 73/356; 116/114.5; 119/1
[58] Field of Search .......... 128/2 H, 1 R, 351, 347, 128/349; 73/356, 357, 358; 116/114.5; 119/1 R, 51

[56] References Cited

U.S. PATENT DOCUMENTS

| | | | |
|---|---|---|---|
| 3,297,020 | 1/1967 | Mathiesen | 119/1 R |
| 3,491,596 | 1/1970 | Dean | 128/2 H |
| 3,722,037 | 3/1973 | Jaeger | 116/114.5 |
| 3,742,958 | 7/1973 | Rundles | 128/347 |
| 3,820,499 | 6/1974 | Kliewer | 116/114.5 |
| 3,872,822 | 3/1975 | Ayres | 73/358 |
| 3,877,411 | 4/1975 | MacDonald | 73/356 |
| 3,889,658 | 6/1975 | Newhall | 128/2 H |
| 3,913,402 | 10/1975 | Doyle | 128/2 H |

*Primary Examiner*—Stephen C. Pellegrino
*Attorney, Agent, or Firm*—Lyon & Lyon

[57] ABSTRACT

An animal information means which utilizes a region behind an animal's ear and adjacent its skull composed of skin, sub-cutaneous fascia and fat in which is formed a cavity, the temperature in the cavity being indicative of the animal's body temperature; the attachment including a temperature actuated warning assembly sensitive to a fever temperature in the animal, the warning assembly having a flanged end arranged to produce a conspicuous visual signal, the warning device being removably received and secured in a retainer assembly adapted to be inserted in the cavity, the retainer having an outer flanged end forming an exposed disk and an inner expansible end, the flanged and expansible end serving to clamp the fascia and skin surrounding the cavity; the retainer also being arranged to receive and secure a shield or guard underlying the flanged end of the retainer and projecting laterally beyond the warning assembly to prevent the surrounding hair growth from covering the warning device, the guard also serving as an identification and a record tag which may be marked to indicate past history of the animal, the retainer sleeve also providing, upon removal of the warning device an access opening into the cavity for insertion of therapeutic substances.

12 Claims, 18 Drawing Figures

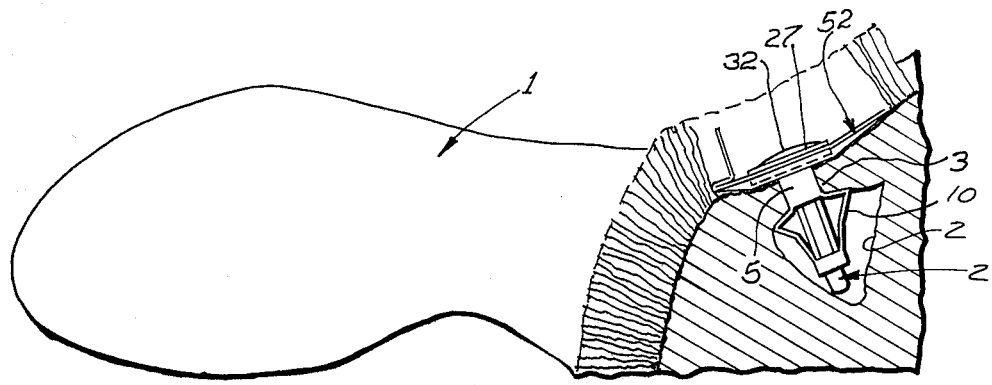
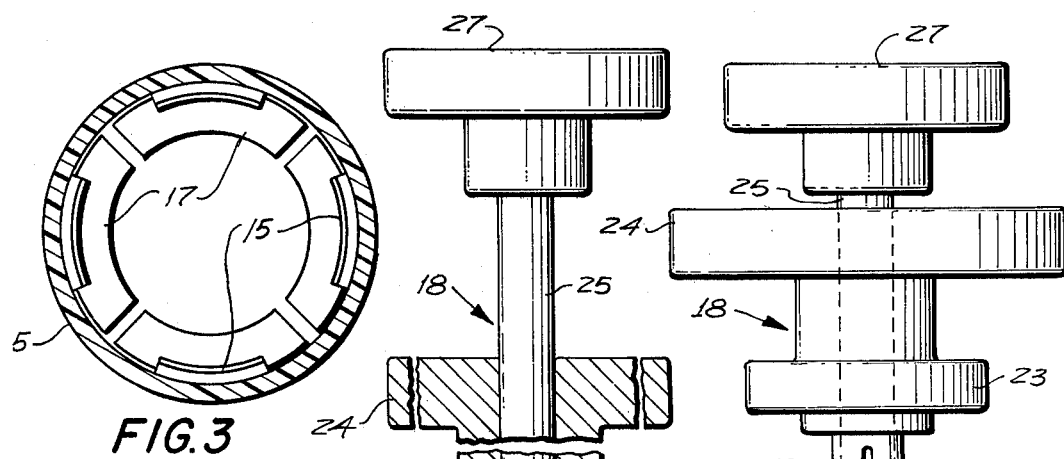
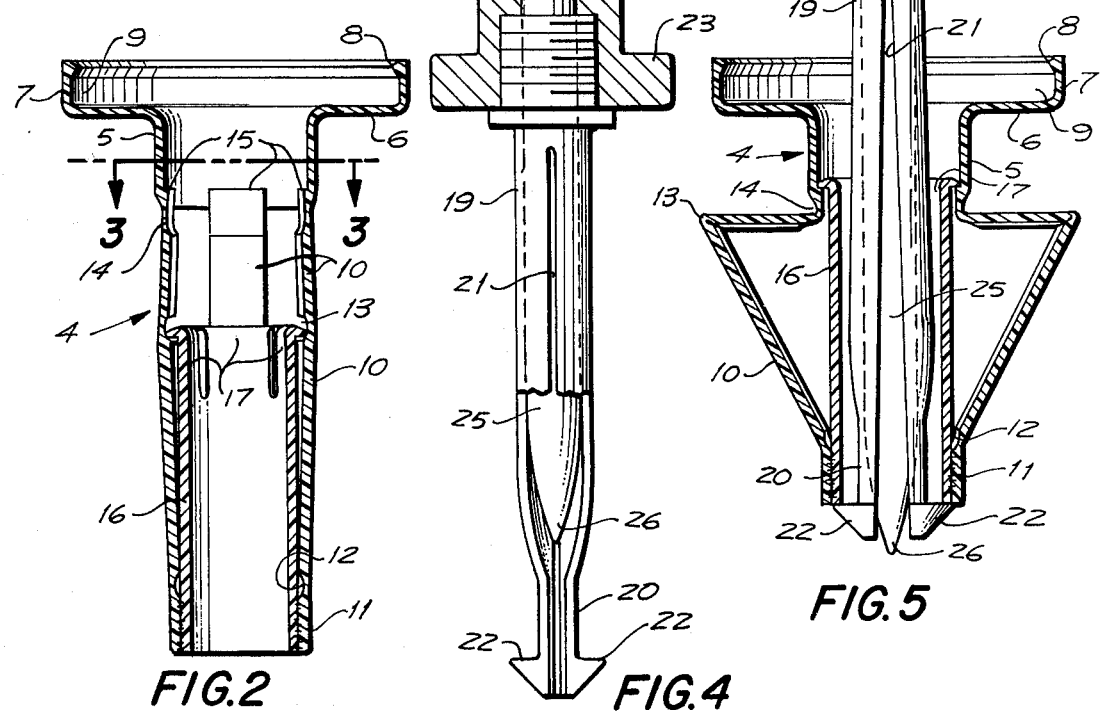

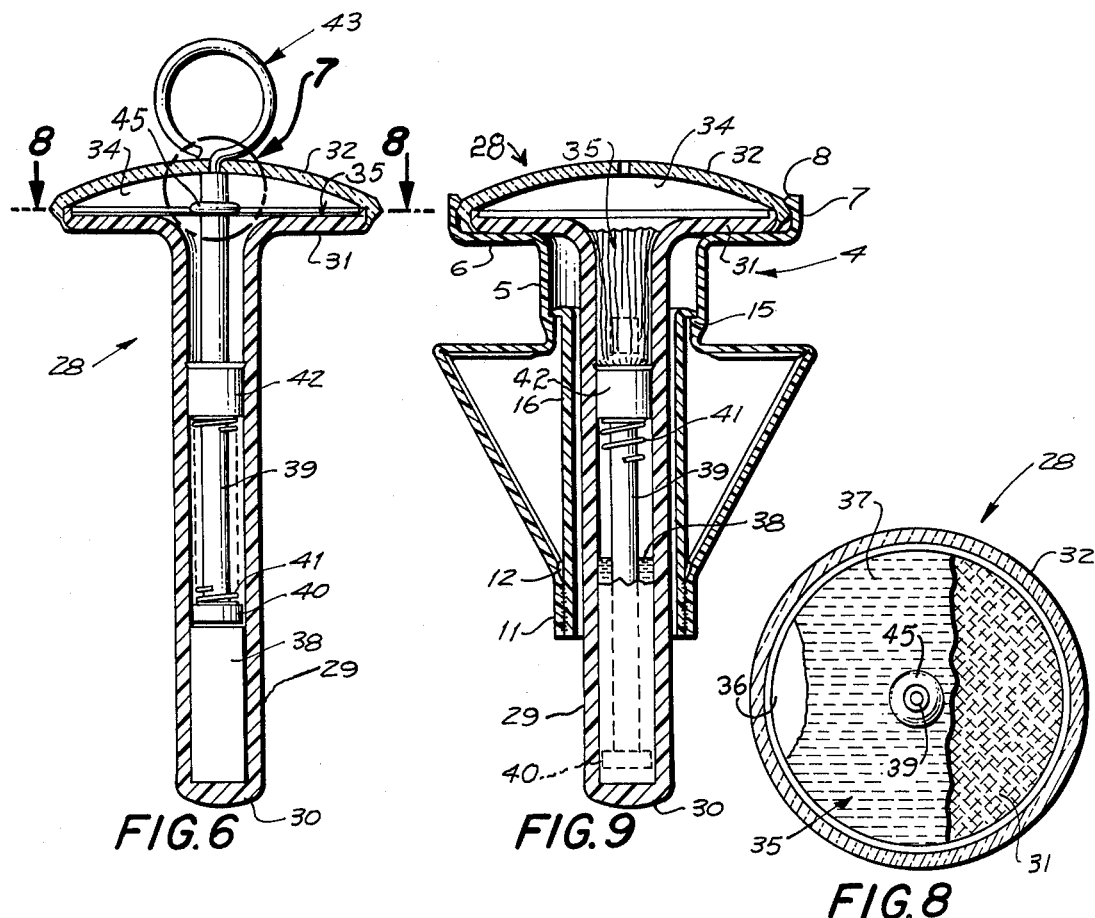
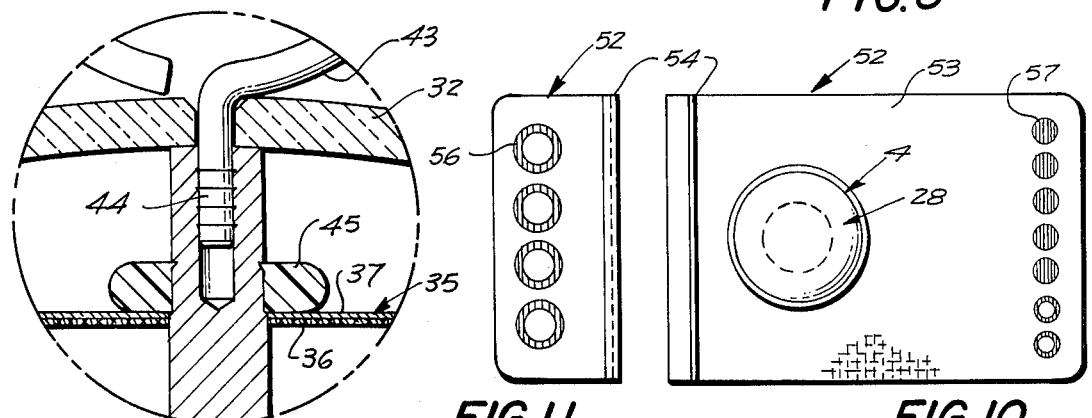
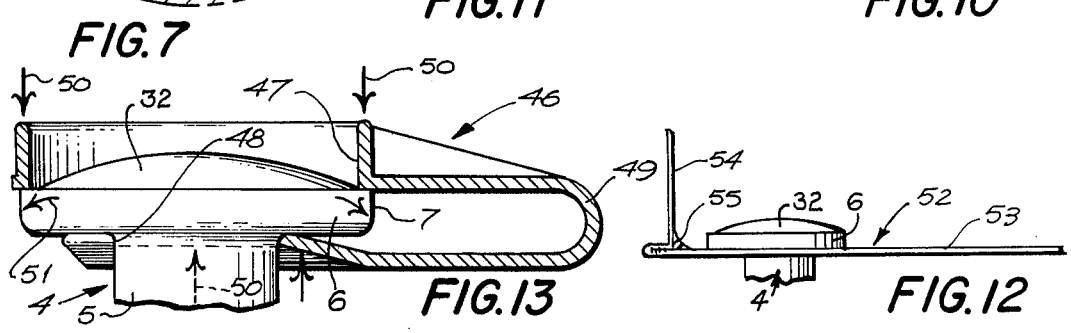

HEAD MOUNTED ANIMAL INFORMATION MEANS

This application is a continuation-in-part of application Ser. No. 580,488, filed May 23, 1975, now abandoned.

BACKGROUND

In the raising and feeding of animals continual vigilance must be maintained to notice any sickness. Sickness is usually accompanied by rise in body temperature. By the time the fever is evident by observation of an animal, the illness has often progressed too far to save the animal and other animals may have become infected. Heretofore, the means of measuring animal body temperature has been in the anal region. Such measurement has required confinement of the animal and thus is expensive. Experimentation has been undertaken in which an anal thermometer is used coupled with an exposed indicator that is permanently attached, for example, to the base of the tail; however, this type of fever indicating means has been limited to feed lot use, and has been extremely expensive.

It has been discovered that there exists a region of an animal's head near the juncture of the back portion of the ear and skull in which is formed a cavity protected by tissue including gristle and hide and further isolated at its lateral and under sides by tissue and bone so that the temperature therein is closely and accurately related to the animal's body temperature, in fact the difference being in the order of 1° F.

This region may be more accurately described as follows: The area bounded cranially by the posterior border of the conchal cartilage and caudally by the anterior border of the cleido-occipitalis muscle. The area is composed of skin, sub-cutaneous fascia and fat. Furthermore, the cavity seems to provide a means whereby certain medicines may be introduced.

SUMMARY

The present invention is directed to a head mounted animal information means, which utilizes an entrance cut into the region previously described, as a "sensor receiving cavity".

A primary object of this invention is to provide a novelly arranged temperature actuated warning assembly forming a part of the animal information means and so constructed as to be inserted in the sensor receiving cavity; the warning device including a conspicuous flanged end having means for producing a conspicuous visual signal when the animal's temperature has risen a predetermined amount.

A further object is to provide, as part of an animal information means, a novel retainer assembly arranged for insertion in the sensor receiving cavity prior to the warning assembly, for removably securing the warning assembly therein; the retainer having a flanged end underlying the flanged end of the warning assembly and also provided with a sleeve portion capable of radial expansion to cooperate with the flanged end of the retainer to secure the retainer in place.

A further object is to provide in an animal information means which includes a novelly arranged guard in sheet form capable of being held between the flanged end of the retainer and the underlying skin of the animal to deflect surrounding hair from extending over and obscuring the warning device.

A further object is to provide an animal information means, as indicated in the previous object, wherein the guard may also serve to identify the animal and provide a record of the past history of the animal.

A further, but primary object is to provide a temperature actuated warning device, particularly adapted for use as a component of an animal information device, wherein a normally solid temperature sensitive material melts at fever temperature to permit axial movement of a rod, the outer end of which is connected to a foldable cover disk initially overlying a highly visible upwardly exposed surface of a flange element; the cover disk when drawn by the rod, exposing the highly visible surface to view; the cover disk having a reflective upper surface to minimize absorption of heat when in its initial flange surface covering position.

A further object is to provide an animal information device having a temperature warning assembly and retainer therefor, in which the warning assembly may be removed to permit introduction of therapeutic substances into the animal.

DESCRIPTION OF THE FIGURES

FIG. 1 is an outline of a calf's ear representing the backside thereof and showing a cut away portion adjacent the skull in which exists a cavity and showing an embodiment of the invention therein.

FIG. 2 is an enlarged longitudinal sectional view of the retainer assembly in its extended position before and during insertion.

FIG. 3 is a further enlarged transverse sectional view taken through 3—3 of FIG. 2.

FIG. 4 is a partial sectional, partial elevational view of the installation tool in its extended position for insertion into the retainer assembly.

FIG. 5 is a partial sectional view, partial side view of the retainer assembly and installation tool the retainer assembly being shown in its position corresponding to that assumed when secured to an animal.

FIG. 6 is an enlarged longitudinal sectional view of the temperature actuated warning assembly in its initial condition corresponding to the condition of the warning assembly when inserted in the retainer assembly.

FIG. 7 is a further enlarged fragmentary sectional view taken within Circle 7 of FIG. 6.

FIG. 8 is a transverse sectional view taken through 8—8 of FIG. 6.

FIG. 9 is a longitudinal sectional view of the warning assembly, within the retainer assembly after the warning assembly has been activated to indicate a fever condition.

FIG. 10 is a plan view of a animal record tag as it would appear when secured in position by the retainer assembly.

FIG. 11 is an end view of the hair guard and animal record tag showing an upstanding end portion.

FIG. 12 is a side view of the hair guard and animal record tag.

FIG. 13 is a fragmentary side view showing the flange ends of the retainer assembly and warning assembly when assembled and illustrating a tool utilized for removal of the warning assembly.

DETAILED DESCRIPTION

Figure 14:
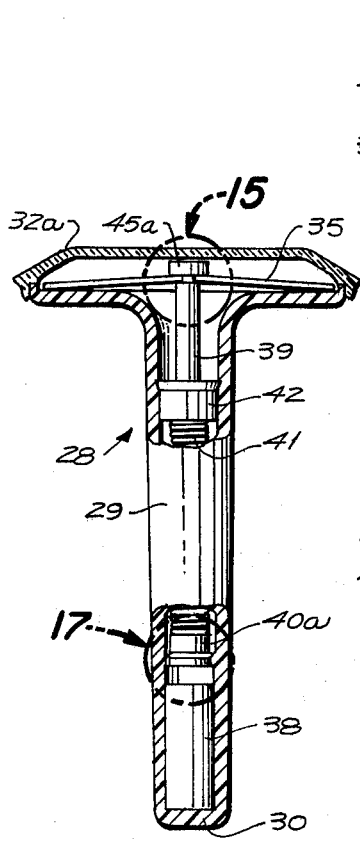
FIG. 14 is a fragmentary side view of a second embodiment of the warning assembly with portions in section.
Figure 15:
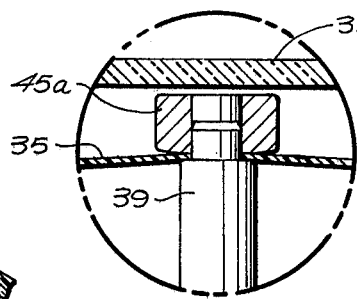
FIG. 15 is an enlarged fragmentary sectional view with portions in elevation, taken within Circle 15 of FIG. 14 showing the warning assembly in its initial condition.
Figure 16:
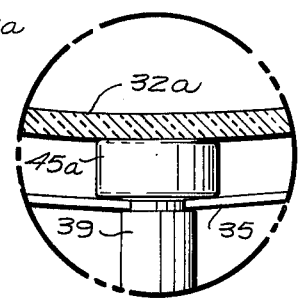
FIG. 16 is an enlarged fragmentary sectional view with portions in section, taken within Circle 15 of FIG. 14 showing the warning assembly after activation just prior to insertion in the animal.
Figure 17:
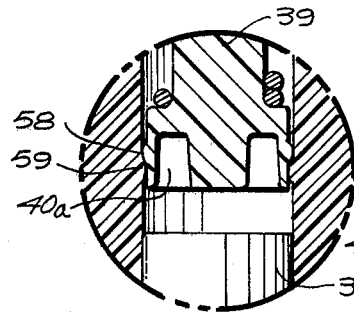
FIG. 17 is an enlarged fragmentary sectional view with portions in section, taken within Circle 17 of FIG. 14 showing the warning assembly in its initial condition.

As indicated in FIG. 1, at the base end of an animal's ear 1, such as a calf's ear, the previously identified sensor receiving cavity 2 is entered by an appropriate surgical tool, piercing through the layer of tissue 3 comprising gristle and hide. Tests have indicated that the temperature in this cavity is reliably related to the temperature of the animal, the temperature in the cavity being about 1° F. lower than the internal rectal temperature of the animal. Also the overlying tissue does not contain sensitive nerves so that it may be pierced by a sharp instrument without discomfort to the animal.

While other regions of an animal for installation of the invention herein described may be used, this region is preferred as it tends to be protected by the corresponding ear and horn.

The animal information means includes a retainer assembly 4 formed of appropriate plastic material and including a sleeve 5, dimensioned to be received in the cavity 2. The upper end of the sleeve is provided with a flange 6 having a peripheral wall 7 provided with an internal retainer bead 8. The flange and wall form a shallow cavity 9.

Extending inwardly from the sleeve 5 is a set, preferably four, of foldable strips 10 joined in their extremities to form a ring 11. Between the ring and sleeve 5 the strips are provided with appropriate weakened zones 12, 13 and 14, so arranged that the strips may be folded outward as shown in FIG. 5 to cooperate with the flange 6 and the clamped tissue 3, as indicated in FIG. 1.

Formed within the sleeve 5 is a set of internal latching shoulders 15. Secured at its lower end within the ring 11 is an inner latching sleeve 16 having latching fingers 17 at its upper end, engageable with the latching shoulders 15.

The retainer assembly initially appears as shown in FIG. 2, in which the out turned portions of the latching fingers 17 are received in the weakened zones 13 so as to hold the strips 10 in a slightly bowed position.

The retainer assembly is secured in place by an installation tool 18, shown in FIGS. 4 and 5. The installation tool includes a tube member 19 having at one end a portion of reduced diameter indicated by 20. The tube member 19 is provided with longitudinal slits 21 forming longitudinal segments that may be forced radially outward. The extremity of the tube member beyond the portion of reduced diameter is provided with outwardly directed pulling fingers 22. The outer end of the tube member is joined to an axial bearing flange 23 dimensioned to bear against the flange 6 of the retainer assembly 4. The bearing flange is joined to a handle disk 24.

The bearing flange and handle disk are tubular to receive a mandrel 25 which extends into the tube member 19 and is provided with a pointed end 26. The opposite end is provided with a handle 27.

The retainer assembly is installed as follows:

First, an appropriate opening is cut through the tissue 3 to provide access to the cavity 2, the sleeve 5 and foldable strips 10 are inserted into the opening. This is done when the retainer assembly is in its initial condition shown in FIG. 2. Before or after positioning the retainer assembly, the installation tool 18 is inserted until the pulling fingers 22 are slightly below the ring 11 and lower end of the latch sleeve 16. This is the condition obtained when the bearing flange 23 rests on the flange 6, as will be noted from the relative positions of the retainer assembly 4 and the installation tool 18 in FIGS. 4 and 5. The mandrel 24 is then thrust forward causing the pointed end 26 to expand the fingers 22 outward so as to underly the sleeve 16 and the ring 11. The tube member 19, bearing flange 23 and handle disk 25 is then withdrawn causing the strips 10 to fold outwardly substantially in the manner shown in FIG. 5. Some kinking or buckling may occur as suggested in FIG. 1 or additional weakened portions may be provided. After the retainer assembly is in place the mandrel 25 19 is withdrawn so that the entire installation tool may be removed.

Referring to FIGS. 6 through 8 there is here illustrated a temperature actuated warning assembly 28 which includes a tube 29 dimensioned to be slidably received by the sleeve 5 and the ring 11 of the installed retainer assembly 4. The end of the tube which becomes the inner end of the assembly is closed as indicated by 30. The other or outer end is provided with a flange 31 joined to a transparent cover 32 by a peripheral sealed connection. The flange 31 and cover 32 form an indicator chamber 34.

The tube 29 and its flanged end 31 are preferably molded of plastic material which may have a fluorescent color or at least a bright hue. The color is preferably orange, but other colors may be used. Also only the outer surface of the flanged end 31 need be colored.

As shown in FIG. 8, overlying the flanged end 31 is a circular shield or cover disk 35, preferably including, as shown in FIG. 7, a sheet 36 of material which is readily flexible and foldable, and a highly reflective coating 37, such as a silver coating, so as to minimize heat absorption.

The inner end of the tube 29 receives a temperature sensitive plug 38 which is normally in a solid condition but is compounded so as to melt at a selected temperature. A temperature is selected which if present in the cavity 2 would indicate a fever condition in the body of the animal. Slidably received in the tube 29 above or outward of the plug 38 is a stem 39 having a flanged end 40. The end 40 is slightly smaller than the tube 29 so that when the plug 38 is in a liquid condition the stem and its flanged end may move downward through the melted plug. Such downward force is provided by a spring 41 which bears against a guide sleeve 42, press fitted in the tube 29.

The stem 29 projects through the shield disk 35 and its outer extremity is held in place by a restraining member 43 having an axial stem 44 which extends through a small opening provided in the cover 32. Above the shield disk 35 there is provided a ring 45 which may be press fitted onto the stem 39.

Operation of the temperature actuated warning assembly 28 is as follows:

Initially the temperature actuated warning assembly is the condition shown in FIG. 6. The restraining member 43 holds the stem 39 against the transparent cover 32 and the flanged end or piston 40 is spaced slightly from the temperature sensitive plug 38.

Prior to use, the warning assembly is stored in an upright position so that should the plug 38 melt and reharden the assembly is not damaged. Once the warning assembly is installed, the restraining member 43 is removed. The warning assembly 28 is placed in the retainer assembly 4 by inserting the tube 29 through the sleeve 5 until the peripheral portion of the cover 32 is snapped within the retainer bead 8, as shown in the upper portion of FIG. 9. In this relative position the inner portion of the tube 29 containing the plug 38 projects beyond the retainer assembly 4, as shown in FIG. 9 and in FIG. 1.

After installation, the warning assembly remains dormant as long as the animal's body temperature is below fever level, that is the upper surface of the flanged end 31 is covered by the shielded disk 35. For purposes of illustration, but not limitation, the surface of the flanged end 31 is shown as orange which is representative of a bright fluorescent color and is covered with the disk 35 having a highly reflective silver hue.

When a fever develops in the animal, the plug 38 liquifies permitting the spring 41 to force the flanged end or piston 40 downward to the liquid plug. This causes the ring 45 to engage and fold the disk 35 as indicated in the upper portion of FIG. 9. In doing so the flanged end 31 becomes fully visible, in addition, the color is reflected to and is picked up by the transparent cover 32 so as to provide a highly visible warning that a fever exists. By selection of the composition comprising the plug 38, the time lapse between the initial fever symptoms and the warning display may be adjusted to meet the most desirable conditions of use; that is, the warning may be such as to avoid premature warnings.

When the warning assembly has once indicated a fever temperature, it must be replaced. This may be accomplished by a removing tool 46, shown in FIG. 13. The tool 46 comprises a peripheral wall 47 which engages the peripheral wall 7 of the retainer assembly 4 and a stem straddling member 48 joined to the ring 47 by a connecting handle loop 49. The member 48 is slipped laterally under the flange 6 while the ring 47 is moved yieldably over the cover 32 until the ring 47 rests on the flange 7. The ring 47 and member 48 are pressed toward each other as indicated by the arrows 50 to snap the periphery of the transparent cover past the retainer bead 8.

If the length of hair surrounding the warning assembly tends to cover the warning assembly, as indicated by FIG. 1, a guard or shield 52 may be interposed between the flange 6 of the retainer assembly 4 and the hair covered skin of the animal to deflect the hair, as shown in FIG. 1. The shield 52 may also serve as a tag providing an animal's record. More specifically, referring to FIGS. 10, 11 and 12, the tag includes a main record portion 53 at one end of which is an upstanding tab 54 which may be held in an upright position for greater visibility by a reinforcing element 55 in the form of a strip molded in place. The upstanding tab 54 serves to carry a serial number indicated by 56 to identify the animal and the main record portion may contain code markings 57 which may be punched. Such markings may be colored for ready identification and the code markings 57 may be used to record the medical history of the animal. In addition coded magnetic information may be provided on a main record portion such as pedigree if such information is significant.

Referring to FIGS. 14 through 18; here illustrated is a second embodiment of the temperature actuated warning assembly which eliminates the perforation in the transparent cover 32. The upper end of the stem 39 is provided with a disk 45a slightly larger than the stem 39 which confronts a transparent cover 32a similar to the cover 32, except that the cover 32a is not perforated and, except for its peripheral portion, is flat so that it may be depressed a limited distance to accomplish a corresponding movement of the stem 39.

The lower end of the stem is provided with a flanged end 40a corresponding to the flanged end 40, except that a small annular rib 58 is provided which engages a small internal mating rib 59. The two ribs initially hold the flanged end 40a clear of the temperature sensitive plug 38 prior to use of the warning assembly.

Figure 18:
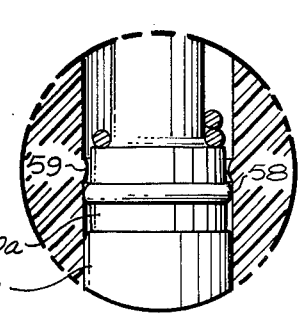
FIG. 18 is an enlarged fragmentary sectional view with portions in section, taken within Circle 17 of FIG. 14, showing the warning assembly after activation just prior to insertion into the animal.

Immediately prior to installing the warning assembly, the cover 32a is depressed moving the rib 58 past the rib 59 to permit the spring 41 to press the flanged end 40 against the temperature sensitive plug 38 as shown in FIG. 18 until the plug melts in response to a fever condition in the animal permitting the disk 35 to be drawn into the tube 29.

The parts which come into contact with the animal may be coated with a turbo-strati form of isotropic carbon or other substance forming a bacterial seal.

As illustrated the cattle information is shown as utilized on a calf, but may also be used on, for example, sheep and or other domestic or semidomestic animals and even if the need arises on some wild animals.

Also the animal information means may be placed on the animal soon after birth and remain throughout the life of the animal, this is particularly true of animals raised for slaughter.

Having fully described our invention it is to be understood that we are not to be limited to the details herein set forth, but that our invention is of the full scope of the appended claims.

We claim:

1. An animal information means adapted for insertion into a cavity cut through the skin and into the subcutaneous fascia of a live animal comprising:
   a. a temperature actuated warning assembly including a fever temperature sensing means, and a fever temperature signalling means;
   b. means for retaining the sensing means in said cavity while exposing the signalling means for view;
   c. the temperature signalling means including an area forming a highly visible surface, a protective transparent element overlying the visible surface, a flexible opaque material interposed between the visible surface and transparent element, and means responsive to the temperature sensing means to remove the opaque material from the highly visible surface thereby to expose said surface to view through said transparent element.

2. An animal information means, as defined in claim 1, wherein:
   a. the fever temperature signalling means further includes a flange having an outwardly exposed, highly visible surface, a tubular portion extending from said flange into the cavity, a readily foldable opaque disk of reflective material initially covering the highly visible surface, and a spring actuated stem means attached to the opaque disk for drawing the opaque disk into the tubular portion thereby to expose the visible surface;

b. the fever temperature sensing means initially restraining the stem means, and adapted to melt at a preselected fever temperature to permit movement of the stem means to draw the opaque disk into the tubular portion.

3. An animal information means, as defined in claim 1, wherein:

a. the retaining means includes an externally disposed flange and a cooperating means within the cavity for securing the flange against the hide of the animal;

b. the temperature signalling means includes a flange overlying the retaining means flange;

c. and a hair guard means is retained under at least one of the flanges and extends radially beyond the temperature signalling means to prevent surrounding hair from restricting the visibility thereof.

4. An animal information means, as defined in claim 3, wherein:

a. the hair guard means is provided with identifying indicia.

5. An animal information means, as defined in claim 3, wherein:

a. the hair guard means includes angularly related portions one of which extends outwardly from the animal for ready visibility and is provided with a code indicator for identifying the animal, and the other portion carries a record of animal history.

6. An animal information means adapted to be mounted in an exposed position and in a penetrating heat receptive relation to an animal, said information means comprising:

a. a temperature sensing means arranged for insertion into the animal in heat receiving relation to the animal;

b. a signalling means overlying the surface of the animal surrounding the inserted temperature sensing means and including a highly visible exposable region of substantial area;

c. a heat reflecting cover for the exposable region;

d. and means interconnecting the temperature sensing means and the cover to remove the cover and expose the highly visible region to view.

7. An animal information means, as defined in claim 6, wherein:

a. the temperature sensing means includes a tubular element and an initially solid member therein meltable at a preselected fever temperature;

b. the cover is formed of readily foldable sheet material;

c. and the interconnecting means is a stem attached at one end to the cover and its other end in contact with the initially solid member and a spring for forcing the stem axially in the tubular element to draw the cover member from the exposable region into the tubular element upon melting of the initially solid member.

8. An animal information means, as defined in claim 6, wherein:

a. a guard is interposed between the signalling means and the surface of the animal, the guard being of such area as to prevent covering the signalling means by animal hair.

9. An animal information means, comprising:

a. a fever warning means received and secured in an opening cut into the animal;

b. the warning means having a stem insertable into the opening for exposure to the temperature therein and a sensing means at the inner end of the stem responsive to a temperature indicative of a fever in the body of the animal;

c. externally exposed means for indicating a fever condition in the body of the animal;

d. means operatively connecting the sensing means and fever indicating means;

e. a retainer means including a flange adapted to removably receive the warning means;

f. a flange provided at the outer end of the warning means dimensioned to be received by the retainer flange;

g. mutually engaging means at the peripheries of the flanges for securing the warning means to the retainer means; and h. means for relatively moving the mutually engaging means to free the warning means from the retainer means.

10. An animal information means as defined in claim 9, wherein:

a. a hair restraining cover and information tab underlies the indicating means.

11. An animal information means as defined in claim 9, wherein:

a. the indicating means includes an area having high visibility and a flexible covering thereover;

b. the sensing means is a meltable element;

c. the connecting means includes a rod extending between the meltable element and the covering;

d. an annular receiving chamber surrounds the end portion of the rod;

e. a spring is positioned to cause movement of the rod relative to the meltable element when the element becomes liquid, thereby to cause the opposite end of the rod to retract into the receiving chamber, draw the covering therein and expose the area of high visibility.

12. An animal information means, comprising:

a. a retainer including a tubular portion for insertion into an animal, a flange positioned on the tubular portion to limit insertion, and means carried in the tubular portion for securing the retainer in place;

b. a warning means including a closed-end tube for insertion through the tubular portion of the retainer, a flange portion overlying the retainer flange, means sensitive to animal fever temperatures disposed in the closed-end tube of the warning means and means carried by the warning means flange responsive to the temperature sensitive means for displaying a fever warning signal.

* * * * *